(12) United States Patent
Williams et al.

(10) Patent No.: US 10,945,616 B2
(45) Date of Patent: Mar. 16, 2021

(54) BLOOD PRESSURE MEASURING SURGICAL INSTRUMENT

(71) Applicant: Covidien LP, Mansfield, MA (US)

(72) Inventors: Justin Williams, Southbury, CT (US); Patrick Mozdzierz, Glastonbury, CT (US); Matthew Eschbach, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 428 days.

(21) Appl. No.: 15/954,538

(22) Filed: Apr. 16, 2018

(65) Prior Publication Data

US 2018/0325394 A1 Nov. 15, 2018

Related U.S. Application Data

(60) Provisional application No. 62/505,168, filed on May 12, 2017.

(51) Int. Cl.
*A61B 5/022* (2006.01)
*A61B 17/29* (2006.01)
(Continued)

(52) U.S. Cl.
CPC ........ *A61B 5/02233* (2013.01); *A61B 5/0215* (2013.01); *A61B 5/02225* (2013.01);
(Continued)

(58) Field of Classification Search
CPC .............. A61B 5/02233; A61B 5/0215; A61B 5/02225; A61B 5/6847; A61B 5/02; A61B 5/021; A61B 5/022; A61B 17/29; A61B 17/115; A61B 2017/00022; A61B 2017/00557; A61B 2017/2926;
(Continued)

(56) References Cited

U.S. PATENT DOCUMENTS 4,109,647 A   8/1978   Stern et al.
4,349,034 A   9/1982   Ramsey, III
(Continued)

FOREIGN PATENT DOCUMENTS

EP    1728475 A2    12/2006
WO   03101277 A2    12/2003
(Continued)

OTHER PUBLICATIONS

European Search Report dated Oct. 17, 2018, corresponding to European Application No. 18171877.6; 8 total pages.
(Continued)

*Primary Examiner* — Daniel L Cerioni
*Assistant Examiner* — Raymond P Dulman
(74) *Attorney, Agent, or Firm* — Carter, DeLuca & Farrell LLP

(57) ABSTRACT

An end effector for determining blood pressure includes a jaw member including a jaw body, a piston coupled to the jaw body and configured to move relative to the jaw body, an inflatable member coupled to the piston, and a pressure sensor associated with the inflatable member. The piston is configured to apply pressure to tissue grasped by the end effector. The pressure sensor is configured to detect pressure fluctuations caused by blood flowing through the grasped tissue.

21 Claims, 5 Drawing Sheets

(51) Int. Cl.
*A61B 5/0215* (2006.01)
*A61B 90/00* (2016.01)
*A61B 5/00* (2006.01)
*A61B 17/00* (2006.01)
*A61B 17/11* (2006.01)
*A61B 5/026* (2006.01)
*A61B 7/04* (2006.01)
*A61B 17/115* (2006.01)

(52) U.S. Cl.
CPC .............. *A61B 17/29* (2013.01); *A61B 90/06* (2016.02); *A61B 5/0261* (2013.01); *A61B 5/6847* (2013.01); *A61B 7/04* (2013.01); *A61B 17/115* (2013.01); *A61B 17/1114* (2013.01); *A61B 2017/00022* (2013.01); *A61B 2017/00057* (2013.01); *A61B 2017/00115* (2013.01); *A61B 2017/00557* (2013.01); *A61B 2017/2926* (2013.01); *A61B 2017/2932* (2013.01); *A61B 2090/065* (2016.02); *A61B 2562/168* (2013.01)

(58) Field of Classification Search
CPC ...... A61B 2017/2932; A61B 2090/064; A61B 2090/065
See application file for complete search history.

(56) References Cited

U.S. PATENT DOCUMENTS

| | | | |
|---|---|---|---|
| 4,360,029 A | 11/1982 | Ramsey, III | |
| 4,862,894 A | 9/1989 | Fujii | |
| 5,395,033 A | 3/1995 | Byrne et al. | |
| 5,518,164 A | 5/1996 | Hooven | |
| 5,722,419 A | 3/1998 | Semmlow et al. | |
| 5,769,791 A | 6/1998 | Benaron et al. | |
| 7,223,279 B2 | 5/2007 | Burbank et al. | |
| 7,229,465 B2 | 6/2007 | Burbank et al. | |
| 7,618,376 B2 | 11/2009 | Kimball | |
| 8,002,795 B2 | 8/2011 | Beetel | |
| 8,073,518 B2 | 12/2011 | Chin | |
| 8,118,206 B2 | 2/2012 | Zand et al. | |
| 8,157,145 B2 | 4/2012 | Shelton, IV et al. | |
| 8,808,311 B2 | 8/2014 | Heinrich et al. | |
| 9,204,830 B2 | 12/2015 | Zand et al. | |
| 2003/0120306 A1 | 6/2003 | Burbank et al. | |
| 2004/0127800 A1 | 7/2004 | Kimball et al. | |
| 2005/0131390 A1 | 6/2005 | Heinrich et al. | |
| 2006/0235314 A1 | 10/2006 | Migliuolo et al. | |
| 2007/0038115 A1 | 2/2007 | Quigley et al. | |
| 2009/0054908 A1 | 2/2009 | Zand et al. | |
| 2011/0144640 A1 | 6/2011 | Heinrich et al. | |
| 2011/0301604 A1* | 12/2011 | Horner | A61B 18/1445 606/52 |
| 2014/0107697 A1 | 4/2014 | Patani et al. | |
| 2014/0135604 A1 | 5/2014 | Cuesta Valentin et al. | |
| 2014/0288386 A1 | 9/2014 | Zand et al. | |
| 2016/0166203 A1* | 6/2016 | Goldstein | A61B 5/02055 600/301 |
| 2017/0367701 A1* | 12/2017 | Park | A61B 17/07207 |
| 2018/0042613 A1* | 2/2018 | Gerosolimo | A61B 17/122 |

FOREIGN PATENT DOCUMENTS

| | | |
|---|---|---|
| WO | 2004071275 A2 | 8/2004 |
| WO | 2006113394 A2 | 10/2006 |
| WO | 2007008057 A1 | 1/2007 |

OTHER PUBLICATIONS

European Search Report dated May 4, 2017, corresponding to European Application No. 16204749.2; 10 total pages.

* cited by examiner

BLOOD PRESSURE MEASURING SURGICAL INSTRUMENT

CROSS-REFERENCE TO RELATED APPLICATIONS

This application claims the benefit of and priority to U.S. Provisional Patent Application No. 62/505,168 filed May 12, 2017, the entire disclosure of which is incorporated by reference herein.

BACKGROUND

1. Technical Field

The present disclosure relates to surgical instruments and, more particularly, to surgical instruments for grasping tissue and determining characteristics of the grasped tissue in preparation for performing various surgical procedures.

2. Background of Related Art

Surgical procedures sometimes involve the cutting and closure of tissue. For example, colorectal surgery sometimes requires anastomosis, which involves resecting a piece of diseased bowel tissue and creating a new connection between presumably two healthy bowel segments. Typically, before performing the anastomosis, the amount of tissue to be resected is estimated using visual indicia of the bowel. A goal of performing the anastomosis is to preserve as much healthy tissue as possible while at the same time removing all of the diseased tissue.

A risk involved in performing an anastomotic procedure is anastomotic leaks. The anastomotic leaks are typically caused by a failure to resect all of the diseased tissue. Current methods used in estimating the amount of tissue to be resected during an anastomotic procedure are sometimes inadequate in preventing all anastomotic leaks.

Accordingly, a need exists for surgical instruments that can sense one or more parameters (e.g., blood pressure) of the bowel tissue to aid a clinician in performing a more successful anastomotic surgical procedure.

SUMMARY

In one aspect of the present disclosure, an end effector for determining blood pressure is provided. The end effector includes a pair of jaw members. A first jaw member of the pair of jaw members includes a jaw body, a piston coupled to the jaw body, a first inflatable member coupled to the piston, and a first pressure sensor associated with the first inflatable member. The piston is configured to move relative to the jaw body to apply pressure to tissue disposed between the pair of jaw members. The first pressure sensor is configured to detect pressure fluctuations caused by blood flowing through tissue disposed between the pair of jaw members.

In some embodiments, the first pressure sensor may be further configured to determine a pressure within the first inflatable member.

In some embodiments, the first jaw member may further include a second inflatable member disposed adjacent the piston such that the second inflatable member moves the piston and the first inflatable member upon being inflated with an inflation medium. The first jaw member may further include a second pressure sensor associated with the second inflatable member. The second pressure sensor may be configured to determine a pressure within the second inflatable member.

In some embodiments, the first pressure sensor may have a first portion in communication with an interior of the first inflatable member, and a second portion in communication with an interior of the second inflatable member. The second portion of the first pressure sensor may be configured to determine a pressure within the second inflatable member.

In some embodiments, the piston may have an elongated configuration and define a hole having the first inflatable member captured therein.

In some embodiments, the first jaw member may further include a housing fixed within the jaw body. The housing may define an opening having the piston movably disposed therein.

In some embodiments, the piston may be configured to move relative to the jaw body between a first position and a second condition, in which the piston protrudes a greater distance relative to the jaw body than in the first position.

In another aspect of the present disclosure, a surgical instrument for determining blood pressure is provided. The surgical instrument includes a handle portion, a shaft coupled to the handle portion, and a pair of jaw members operably coupled to the shaft. A first jaw member of the pair of jaw members includes a jaw body, a piston coupled to the jaw body, a first inflatable member coupled to the piston, and a first pressure sensor associated with the first inflatable member. The piston is configured to move relative to the jaw body to apply pressure to tissue disposed between the pair of jaw members. The first pressure sensor is configured to detect pressure fluctuations caused by blood flowing through tissue disposed between the pair of jaw members.

In some embodiments, the first jaw member may further include a second inflatable member disposed adjacent the piston such that the second inflatable member moves the piston and the first inflatable member upon being inflated with an inflation medium. The piston may be coupled to the second inflatable member such that the piston moves away from the jaw body in response to an expansion of the second inflatable member and the piston moves toward the jaw body in response to a contraction of the second inflatable member.

In some embodiments, the surgical instrument may further include a processor in communication with the first pressure sensor. The processor may be configured to calculate a blood pressure of tissue grasped by the pair of jaw members based on the pressure fluctuations detected by the first pressure sensor.

It is contemplated that the surgical instrument may be laparoscopic. The pair of jaw members may be movable relative to one another between spaced and approximated positions in response to an actuation of the handle portion.

In yet another aspect of the present disclosure, a method of determining local blood pressure is provided. The method includes positioning tissue between a pair of jaw members of a surgical instrument. A piston having a first inflatable member associated therewith is moved relative to a jaw body of a first jaw member of the pair of jaw members, thereby applying pressure on the tissue with at least one of the piston or the first inflatable member. Pressure fluctuations in the first inflatable member are measured with a first pressure sensor associated with the first inflatable member. The local blood pressure of the tissue is determined using the measured pressure fluctuations.

Some methods may further include expanding a second inflatable member of the first jaw member to move the piston and the first inflatable member into engagement with the tissue.

Some methods may further include determining a pressure within the second inflatable member as the piston is being moved. The local blood pressure of the tissue may be determined using both the measured pressure fluctuations in the first inflatable member and the measured pressure within the second inflatable member.

Some methods may further include moving the piston and the first inflatable member toward the jaw body to reduce the applied pressure on the tissue. The first pressure sensor may measure the pressure fluctuations as the pressure applied on the tissue is reduced.

Some methods may further include contracting the second inflatable member to move the piston and the first inflatable member toward the jaw body, thereby reducing the pressure applied on the tissue by the piston.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
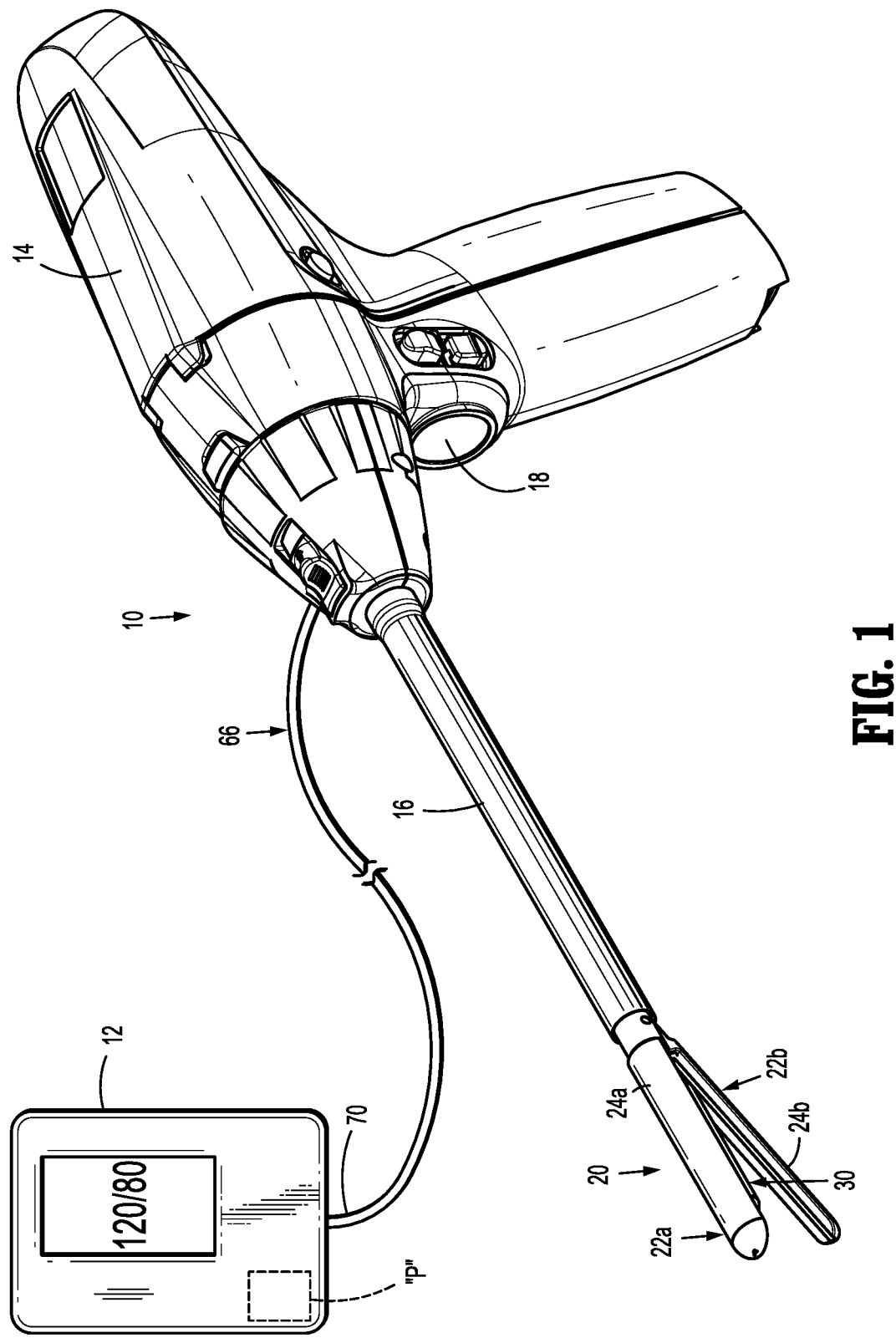
FIG. 1 is a perspective view of one embodiment of a surgical instrument including an end effector for grasping tissue and determining a local blood pressure of the grasped tissue.

Embodiments of the presently disclosed surgical instruments and end effectors thereof will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

The present disclosure is directed to a tissue grasper for measuring blood pressure in tissue, such as bowel tissue, using the oscillometric method. The tissue grasper includes a pair of jaw members for grasping tissue therebetween, a first balloon member disposed within a movable piston, and a second balloon member. The second balloon member is expanded to force the piston and the first balloon member into engagement with tissue to apply pressure on the grasped tissue. The first balloon member includes a sensor that detects pressure fluctuations (i.e., oscillations) caused by pressure pulses from blood flowing through the grasped tissue, and the second balloon member includes a sensor that measures the air pressure within the second balloon member. The second balloon member is first inflated to a pressure at which occlusion of blood flow through the tissue occurs. The second balloon member is gradually deflated to reduce the amount of pressure applied on the tissue. As the pressure applied is reduced to at or below the occlusion pressure, the first pressure sensor senses the oscillations created by the pulsatile flow of blood through the grasped tissue, and the second sensor measures the air pressure within the second inflatable member. The blood pressure may be calculated using the measured oscillations in air pressure in the first balloon member and the measured pressure in the second balloon member.

The basis for the oscillometric method of measuring blood pressure is disclosed in U.S. Pat. Nos. 4,349,034 and 4,360,029 both to Ramsey, III, the entire contents of which are incorporated by reference herein. As disclosed by Ramsey, III, the oscillometric method of measuring blood pressure includes applying an inflatable cuff around an extremity of a patient's body and inflating the cuff to a pressure that exceeds the patient's systolic pressure such that no blood flows through the artery of the tissue (i.e., the artery is occluded). The pressure within the cuff is incrementally reduced while a pressure sensor in communication with the interior of the cuff tracks the pressure therein. As the cuff is deflated below the systolic pressure, blood begins to flow through the artery creating vibrations or pulses in the arterial wall that are transferred to the cuff causing slight pressure variations within the cuff. These pressure variations within the cuff are detected by the pressure sensor. The pressure sensor produces an electrical signal which represents the pressure within the cuff throughout the measurement process, and the sensed pulsatile vibrations at each discreet pressure within the cuff. These pulsatile vibrations are called "oscillation complexes" or "oscillations."

Local blood pressure may be estimated based on the oscillation complexes measured by the pressure sensor. For example, peak pulse amplitudes ("PPA") may be determined for each oscillometric complex. The PPA increases as the cuff pressure is reduced until a peak amplitude is reached. Once the peak amplitude is reached, the PPA begins to decrease with further reductions in cuff pressure. The cuff pressure at which the oscillations have a maximum value is representative of the patient's mean arterial pressure ("MAP"). The systolic and diastolic pressures can be derived either as predetermined fractions of MAP, or by more sophisticated estimating techniques using direct processing of the oscillation complexes.

FIGS. 1-3A illustrate a surgical instrument 10 for measuring local blood pressure of tissue grasped between a pair of jaw members 22a, 22b of the surgical instrument 10 using the oscillometric method. In embodiments, the surgical instrument 10 may be configured to measure blood pressure using other methods, such as, for example, the auscultatory method. The surgical instrument 10 may include a visual display unit 12 for displaying the blood pressure determined by the surgical instrument 10.

The surgical instrument 10 generally includes a handle portion 14, an elongated shaft 16, and an end effector 20. The handle portion 14 of the surgical instrument 10 may be power-operated or manually-operated. An actuation of a switch or button 18 of the handle portion 12 is configured to effect closing of the jaw members 22a, 22b of the end effector 20 to grasp tissue disposed between the jaw members 22a, 22b. The handle portion 14 may include a processor for transforming an actuation of the switch 18 into a closing of the jaw members 22a, 22b.

The end effector 20 is detachably coupled to a distal portion of the elongated shaft 16 or, in some embodiments, may be fixedly coupled to the distal portion of the elongated shaft 16. The end effector 40 includes the pair of opposing jaw members 22a, 22b which are movable between spaced and approximated positions. A first jaw member 22a of the end effector 20 includes a jaw body 24a fixedly coupled to the distal portion of the elongated shaft 16, and a second jaw member 22b of the end effector 20 includes a jaw body 24b pivotably coupled to the distal portion of the elongated shaft 16. In embodiments, one or both of the jaw bodies 24a, 24b may be movably coupled to the distal portion of the elongated shaft 16.

The first jaw member 22a includes a blood pressure sensing assembly 30 housed within the jaw body 24a thereof. In embodiments, the blood pressure assembly 30 may be housed within the jaw body 24b of the second jaw member 22b rather than the first jaw member 22a. The blood pressure assembly 30 is in communication with a processor "P" disposed within the visual display unit 12. In some embodiments, the processor "P" may instead be disposed within the handle portion 14 of the surgical instrument 10. The processor "P" may be operably connected to a memory, which may include transitory type memory (e.g., RAM) and/or non-transitory type memory (e.g., flash media, disk media, etc.). The processor "P" may include software for running a blood pressure measurement sequence. Those skilled in the art will appreciate that the processor "P" may be substituted by using any logic processor (e.g., control circuit) adapted to perform the calculations and/or set of instructions described herein including, but not limited to, field programmable gate arrays, digital signal processor, and combinations thereof.

Figure 2:
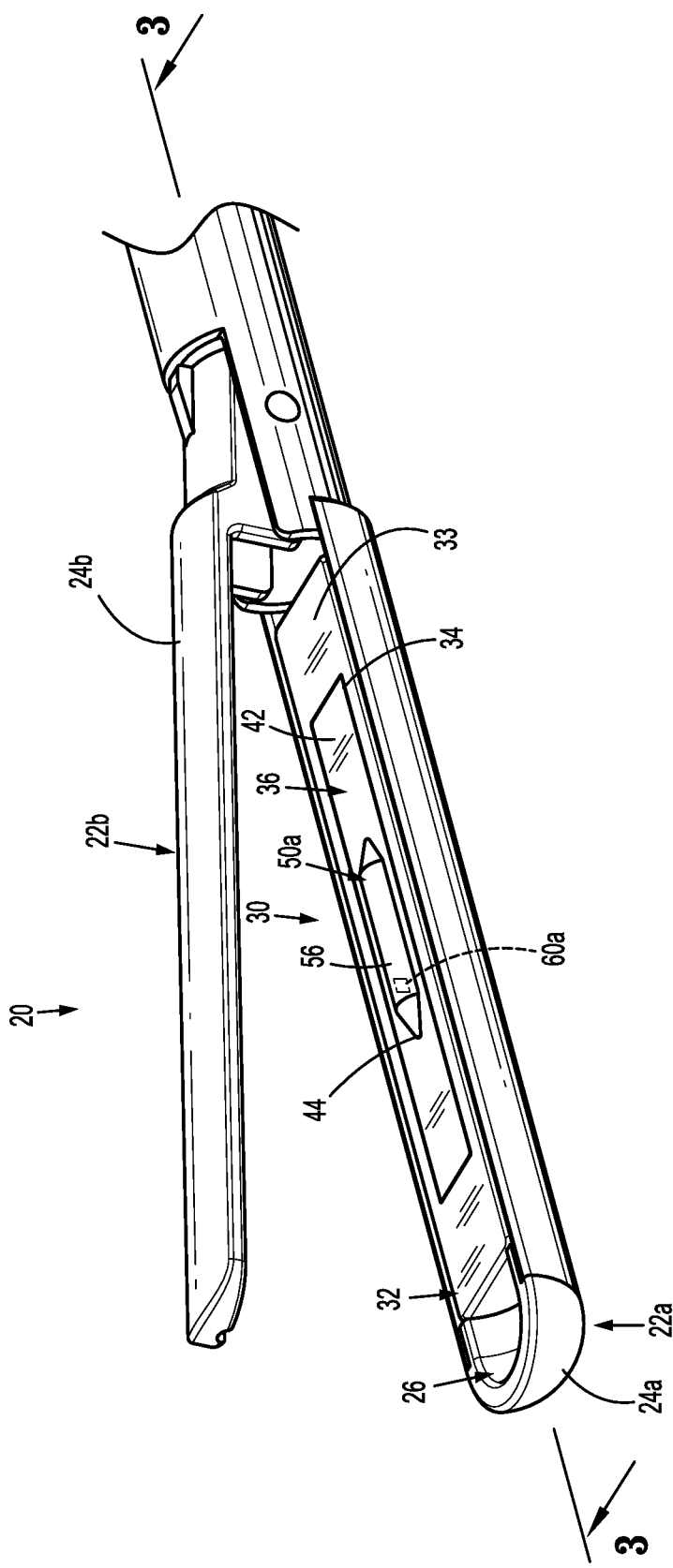
FIG. 2 is an enlarged perspective view of the end effector of FIG. 1 illustrating a blood pressure sensing assembly.
Figure 3:
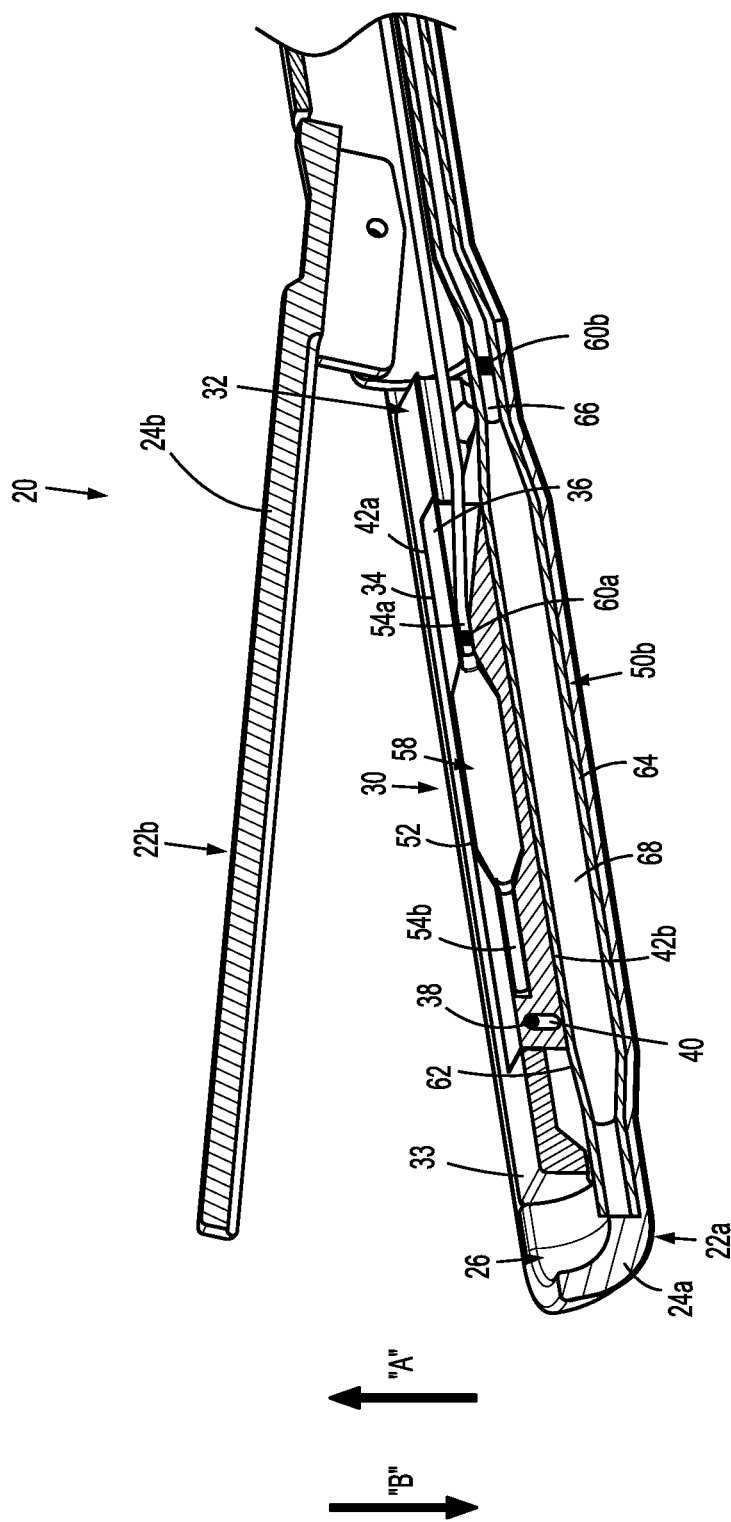
FIG. 3 is a cross-sectional view, taken along line 3-3 in FIG. 2, of the end effector illustrating components of the blood pressure sensing assembly.
Figure 3A:
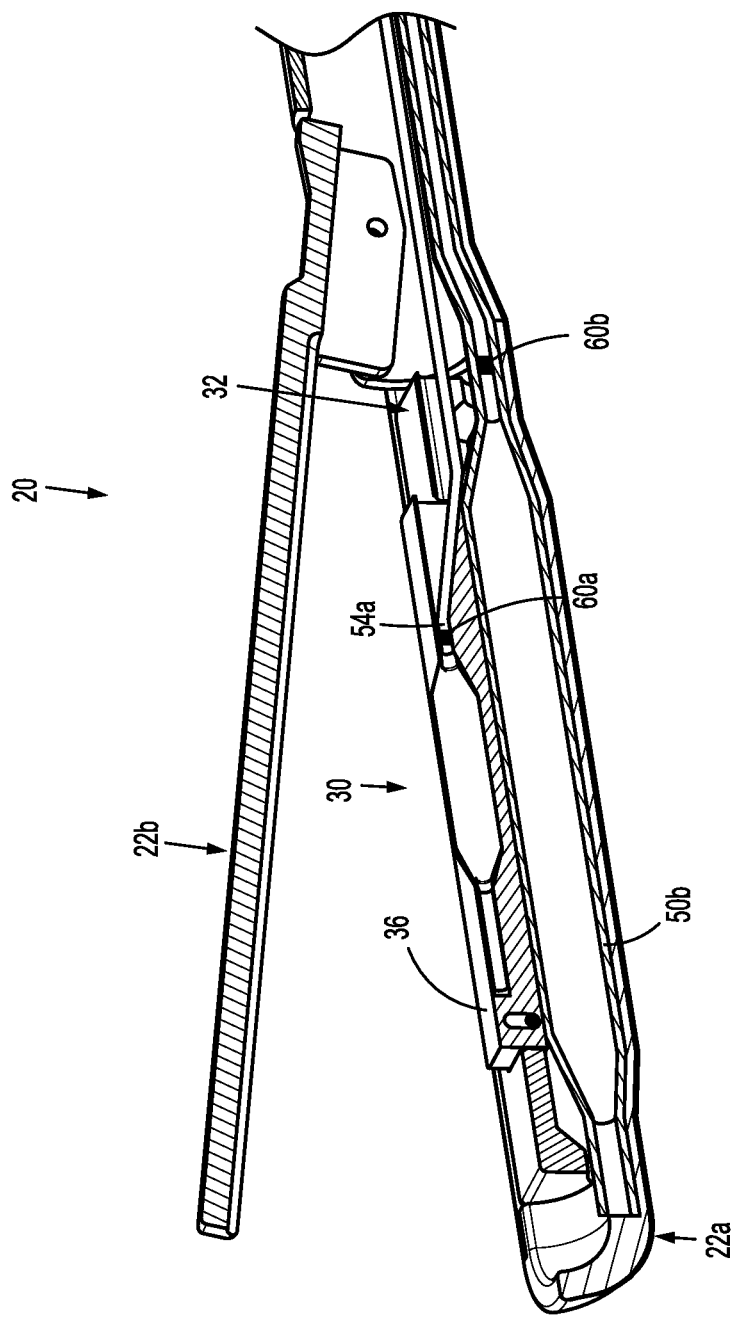
FIG. 3A is a perspective view of the cross-section of the end effector of FIG. 3 illustrating the blood pressure sensing assembly in an expanded configuration.

With reference to FIGS. 2, 3, and 3A, the blood pressure sensing assembly 30 generally includes a piston or block 36, two inflatable members 50a, 50b, and two sensors 60a, 60b. The first jaw member 22a includes a piston housing or piston sleeve 32 fixedly disposed within a cavity 26 defined in the jaw body 24a. The piston housing 32 defines an elongate channel 34 having the piston 36 disposed therein. The piston 36 is movable within the elongate channel 34 of the housing 32. The piston housing 32 may include a pin 38 projecting into the elongate channel 34 thereof. The pin 38 extends into a slot 40 defined partially through a distal end of the piston 36 to prevent the piston 36 from dislodging from the piston housing 32. In particular, as the piston 36 moves or slides away from the jaw body 24a in a direction indicated by arrow "A" in FIG. 3, the pin 38 of the housing 32 rides in the slot 40 of the piston 36 until the pin 38 contacts an end wall of the slot 40 of the piston 36, thereby preventing any further travel of the piston 36.

The piston 36 has a substantially rectangular configuration, but in some embodiments, the piston 36 may assume any suitable shape, such as, for example, square, triangular, oblong, circular, or the like. The piston 36 defines a planar tissue-contacting surface 42a that is coplanar with a tissue-oriented surface 33 of the housing 32 when the piston 36 is in a retracted position, as shown in FIG. 2. When the piston 36 protrudes from the housing 32, the tissue-contacting surface 42a of the piston 36 is disposed upward of or above the tissue-oriented surface 33 of the housing 32. The tissue-contacting surface 42a of the piston 36 defines a hole 44 therein dimensioned for receipt of the first inflatable member 50a of the blood pressure sensing assembly 30.

The first inflatable member 50a is fixedly disposed within the hole 44 of the piston 36 such that the first inflatable member 50a moves with the piston 36 as the piston 36 slides relative to the jaw body 24a between retracted and deployed states. The first inflatable member 50a has a disc or saucer-shaped main body 52 and proximal and distal tubes 54a, 54b extending from opposite ends of the main body 52. In embodiments, the main body 52 of the first inflatable member 50a may assume a variety of shapes, such as, for example, cylindrical, rectangular, or the like. The main body 52 of the first inflatable member 50a has a top or outer surface 56 that is substantially flush with the tissue-contacting surface 42a of the piston 36. In some embodiments, the top surface 56 of the main body 52 of the first inflatable member 50a may protrude outwardly of the tissue-contacting surface 42a of the piston 36.

The first inflatable member 50a may be fabricated from a biocompatible material such as natural or synthetic elastomers, natural or synthetic rubbers and silicone materials, and/or compliant polyurethanes. The main body 52 of the first inflatable member 50a defines a hollow inner chamber or void 58 that receives an inflation media that changes or moves the main body 52 of the first inflatable member 50a from a collapsed configuration to an expanded configuration. The proximal tube 54a may extend proximally through the elongated shaft 16 (FIG. 1) to couple to a pump (not shown) disposed in the visual display unit 12 for adjusting the amount of inflation media in the first inflatable member 50a and, in turn, the pressure in the first inflatable member 50a. In other embodiments, the first inflatable member 50a may not be connected to the pump such that the first inflatable member 50a has a fixed amount of inflation media therein.

The first inflatable member 50a further includes a pressure sensor 60a disposed in the proximal tube 54a for sensing air pressure fluctuations (e.g., oscillations) within the first inflatable member 50a. In embodiments, the pressure sensor 60a may be disposed in any suitable location within the first inflatable member 50a, such as the main body 52. The pressure sensor 60a may be a piezoelectric transducer, a piezoresistive strain gauge, an electromagnetic optical sensor, or any other suitable pressure sensor that detects pressure variations within the first inflatable member 50a caused by pulse waves generated by the pulsatile flow of blood through an artery (e.g., oscillations).

In embodiments, in addition to the pressure sensor 60a being configured to sense oscillations, the pressure sensor 60a may also be configured to measure the pressure (e.g., air pressure) within the first inflatable member 50a. In other embodiments, the first pressure sensor 60a may be a perfusion sensor, for example, a Doppler flow sensor, configured to measure local perfusion (e.g., blood flow) through tissue grasped by the jaw members 22a, 22b. The pressure sensor 60a may measure perfusion of the grasped tissue on the basis of known techniques, such as Laser-Doppler Flowmetry ("LDF"), measuring light scattering, and/or measuring absorption of light from one or more LED's or other light sources. For a detailed description of LDF technology, reference may be made to U.S. Pat. Nos. 4,109,647 and 4,862,894, the entire contents of each of which are incorporated by reference herein.

In still other embodiments, instead of the first inflatable member 50a having a pressure sensor, the first inflatable member 50a may include a stethoscope head, an ultrasound pickup, or a microphone for receiving auditory signals generated by blood flowing through tissue. It is contemplated that any of these sensors may be disposed within the first inflatable member 50a, on the first inflatable member 50a, on the tissue-contacting surface 42a of the piston 36, or at any other suitable location of the end effector 20.

The first pressure sensor 60a is in communication, via lead wires or wireless connection, with the processor "P" of the visual display unit 12, which receives the pressure fluctuation data collected by the first pressure sensor 60a. Upon the first pressure sensor 60a measuring the pressure oscillations in grasped tissue, the first pressure sensor 60a transmits the data to the processor "P." In some embodiments, the first pressure sensor 60a may also be in communication, via lead wires or wireless connection, with a computing device or processor (not shown) such as an oscilloscope, which processes the information collected by the first pressure sensor 60a. The computing device (e.g., an oscilloscope) may also be in communication, via lead wires or wireless connection, with the visual display unit 12 to send the processed information related to the blood pressure to a display screen so that the display screen can display the blood pressure.

With continued reference to FIGS. 2, 3, and 3A, the second inflatable member 50b of the blood pressure sensing assembly 30 has a main body 64 and a tube 66 extending from a proximal end of the main body 64. The main body 64 of the second inflatable member 50b defines a hollow inner chamber or void 68 that receives an inflation media (e.g., air) that changes or moves the main body 64 of the second inflatable member 50a from a collapsed configuration, in which the main body 64 is substantially flat and rectangular, to an expanded configuration, in which the main body 64 is larger than in the collapsed configuration and assumes a bulbous configuration. In some embodiments, the main body 64 of the second inflatable member 50b may be configured to assume any suitable shape when in the expanded configuration, such as, for example, rectangular, dome-shaped, elliptical, oblong, tubular, square, triangular, cylindrical, rod-shaped, or the like. The tube or hose 66 of the second inflatable member 50b is in fluid communication with the hollow inner chamber 68 of the main body 64 and may extend proximally from the main body 64 through the elongated shaft 16 and out of the surgical instrument 10. The tube 66 may have an end 70 (FIG. 1) coupled to a source of inflation media, such as, for example, a pump (not explicitly shown), for delivering a liquid and/or gas into the hollow inner chamber 68 of the second inflatable member 50b.

The main body 64 of the second inflatable member 50b is captured within the cavity 26 of the jaw body 24a and may be fixed at its distal end to a distal end of the jaw body 24a. The main body 64 of the second inflatable member 50b is disposed below or under the piston 36 and in abutting engagement with a bottom surface 42b of the piston 36. As such, an expansion of the second inflatable member 50b effects movement or sliding of the piston 36 and the attached first inflatable member 50a away from the jaw body 24a and toward clamped tissue in the direction indicated by arrow "A" in FIG. 3. In embodiments, the first inflatable member 50a may extend below the bottom surface 42b of the piston 36 to contact a top surface 62 of the second inflatable member 50b.

The top surface 62 of the second inflatable member 50b may be fixed to the bottom surface 42b of the piston 36 such that contraction of the second inflatable member 50b retracts the piston 36 and the first inflatable member 50a toward the jaw body 24a in the direction indicated by arrow "B" in FIG. 3. The top surface 62 of the second inflatable member 50b may be attached to the bottom surface 42b of the piston 36 and/or the first inflatable member 50a via an adhesive, a hook and loop fastener, a suture, or the like. In other embodiments, instead of the first and second inflatable members 50a, 50b being attached to one another to facilitate retraction of the first inflatable member 50a, a biasing member (not shown) may be provided that resiliently biases the piston 36/first inflatable member 50a toward a retracted position within the jaw body 24a such that even in the absence of an outward pressure applied on the piston 36/first inflatable member 50a by the second inflatable member 50b, the piston 36/first inflatable member 50a are still biased toward the retracted state.

The second inflatable member 50b further includes a second pressure sensor 60b (e.g., a piezoresistive pressure sensor, a capacitive pressure sensor, a MEMS device, etc.) disposed within the proximal tube 66 thereof. In embodiments, the second pressure sensor 60b may instead be disposed within the main body 64 of the second inflatable member 50b. The second pressure sensor 60b is configured to measure the pressure (e.g., air pressure) within the second inflatable member 50b.

Since the pressure within the second inflatable member 50b is responsible for forcing the piston 36 and the first inflatable member 50a into engagement with tissue, the pressure within the second inflatable member 50b is substantially similar to and/or directly correlated with the pressure experienced on the arteries within tissue grasped between the jaw members 22a, 22b. Thus, by knowing the pressure within the second inflatable member 50b, via the second pressure sensor 60b, the pressure applied on grasped tissue by the piston 36/first inflatable member 50a will be known. After the second pressure sensor 60b measures the clamping pressure applied to the grasped tissue, the second pressure sensor 60b transmits the measurement data to the processor "P," which together with the pressure fluctuation data determined by the first pressure sensor 60a, calculates blood pressure and displays the measurement on the display screen of the visual display unit 12, as will be described in further detail below.

In operation, the surgical instrument 10 may be used in a surgical procedure in which tissue is to be stapled, for example, an anastomotic surgical procedure, to gather various data about the subject tissue prior to effecting stapling. In some anastomotic surgical procedures, unhealthy or diseased bowel tissue is resected and the ends of the remaining healthy segments of bowel are stapled together to recreate a continuous bowel. Prior to stapling the ends of the separate bowel segments to one another, the viability of the ends of the separate bowel segments should be assessed in order to predict the likelihood of post-surgery anastomotic leaks or other adverse outcomes. It has been found that local blood pressure of bowel segments is an indicator of tissue viability. Accordingly, a clinician may make use of the blood pressure measuring surgical instrument 10 of the present disclosure to aid in making this viability assessment.

In use of the surgical instrument 10, the end effector 20 of the surgical instrument 10 is positioned through an access port (not shown) to gain entry to a surgical site in a minimally invasive manner. With the second inflatable member 50b of the blood pressure sensing assembly 30 in a collapsed or substantially un-inflated state, tissue is disposed between the tissue-contacting surface 42a of the piston 36 of the first jaw member 22a and the tissue contacting surface of the second jaw member 22b.

With the tissue disposed between the jaw members 22a, 22b, the pump of the visual display unit 12 conveys an inflation media (e.g., air) into the hollow inner chamber 68 of the second inflatable member 50b via the tube 66 to expand the second inflatable member 50b, as shown in FIG. 3A. As the second inflatable member 50b expands, the second inflatable member 50b applies an upward-oriented force on the piston 36 to raise the piston 36 relative to the jaw body 24a of the first jaw member 22a in the direction indicated by arrow "A." Since the first inflatable member 50a is captured within the piston 36, the first inflatable member 50a rises with the piston 36 relative to and away from the jaw body 24a to apply pressure on the grasped tissue.

Continued expansion of the second inflatable member 50b increases the distance the piston 36/first inflatable member 50a projects from the jaw body 24a and, in turn, increases the clamping pressure on the tissue. The processor "P" may be pre-programmed to expand the second inflatable member to a threshold pressure known to occlude an artery (e.g., a pressure that exceeds the systolic pressure of any patient).

Upon reaching the threshold pressure, the inflation media (e.g., air) is gradually removed from the second inflatable member 50b in incremental steps to contract the second inflatable member 50b. As the second inflatable member 50b contracts, the piston 36 and the associated first inflatable member 50a retract back toward the jaw body 24a of the first jaw member 22a, in the direction indicated by arrow "B," to reduce the clamping pressure on the tissue. The surgical instrument 10 may be pre-programmed to reduce the clamping pressure at a predetermined rate via deflation of the second inflatable member 50b.

As the pressure applied to the grasped tissue is gradually reduced, the first pressure sensor 50a continuously monitors any pressure fluctuations (e.g., oscillations) generated by blood flowing through the arteries in the grasped tissue. Before the clamping pressure drops below the systolic pressure of the patient, the first pressure sensor 60a should not detect any oscillations since no blood is flowing through the arteries at this clamping pressure. However, the artery may be emitting slight percussion pulses due to the blood hitting the occluded artery in pulses. These slight percussive pulses are so low in force that the vibrations they induce are absorbed by the movable piston 36, thereby damping their impact on the first pressure sensor 60a. In this way, these damped percussive pulses will be too small for the first pressure sensor 60a to detect, which may otherwise be confused by the processor "P" as oscillations from flowing blood rather than percussion pulses from an occluded artery.

The moment the pressure applied on the tissue by the end effector 20 falls below the systolic pressure of the patient, blood begins to flow through the clamped tissue and will produce the oscillations described above. The first pressure sensor 60a in the first inflatable member 50a detects and measures these oscillations and transfers the measurement data to the processor "P." While the clamping pressure is gradually reduced, the second pressure sensor 60b in the second inflatable member 50b continuously monitors the pressure within the second inflatable member 50b and sends this pressure measurement data to the processor "P."

Reduction of the clamping pressure, via deflation of the second inflatable member 50b, is continued until the pressure within the second inflatable member 50b falls below a threshold pressure corresponding to the diastolic pressure of any patient. In embodiments, instead of gradually decreasing the clamping pressure on the tissue by deflating the second inflatable member 50b, the jaw members 22a, 22b may be gradually pivoted away from one another. The processor "P" uses the data collected by the first and second pressure sensors 60a, 60b to compute the local blood pressure in the grasped tissue using any suitable algorithm. In embodiments, the processor "P" may be configured to compute the blood pressure from the measurements made by the first and second pressure sensors 60a, 60b using the process described in U.S. Pat. No. 4,360,029, the entire contents of which are incorporated by reference herein. Upon the surgical instrument 10 calculating the blood pressure, the visual display unit 12 displays the calculated blood pressure on the display screen for the clinician to view.

The blood pressure determined using the above-noted technique may be used to assess the viability of the grasped tissue by, for example, comparing the measured local blood pressure with a known local blood pressure associated with healthy or viable tissue. Additionally or alternately, the measured local blood pressure may be used in combination with other measurements, for example, a systemic blood pressure reading, to aid in making the determination of the viability of the tissue. The systemic blood pressure may be taken using any suitable device, for example, a blood pressure cuff, applied to any suitable body portion of the patient, for example, an arm of the patient. An index may be calculated by taking a ratio of the local blood pressure measured by the surgical instrument 10 and the systemic blood pressure taken using the blood pressure cuff. The index may be calculated by the computing device in the visual display unit 12 and displayed as a number on the display screen.

The calculated index may be predictive of whether an anastomotic leak may occur and/or the grade of an anastomotic leak. As such, a clinician can use the index to make a determination on whether the two ends of the presumed healthy bowel segments are healthy enough to be stapled together or whether more tissue needs to be resected. For example, the calculated index may be compared to a known index that is associated with healthy tissue.

In some embodiments, the surgical instrument 10 may not include the display 12, and instead, the surgical instrument 10 may be configured to be connected to or be in communication with another type of display, for example, a tablet, a cell phone, a computer monitor, a laptop, or any suitable display device. The surgical instrument 10 may be connected to any of the aforementioned display devices via USB wires, Wi-Fi, or the like. In other embodiments, the visual display unit 12 may be integrated into the handle portion 14 of the surgical instrument 10 rather than being an auxiliary component.

In some embodiments, the second inflatable member 50b may be replaced with a powered actuator (e.g., a pusher, a sled, a screw, etc.) operably coupled to the piston 36 to selectively raise the piston 36 and the first inflatable member 50a relative to the jaw body 24a. The motorized actuator may be associated with a pressure sensor that senses the amount of pressure applied to the piston 36 by the motorized actuator. The pressure sensor may be disposed on one or both of the tissue-contacting surfaces of the first and second jaw members 22a, 22b. In this alternate embodiment, it is also contemplated that the first inflatable member 50a may include each of the first and second pressure sensors 60a, 60b.

The surgical instrument 10 or components thereof may be configured to be incorporated into a robotic surgical system (not shown). The robotic surgical system is powered locally or remotely, and has electronic control systems localized in a console or distributed within or throughout the robotic surgical system. The robotic surgical system permits a clinician to remotely manipulate the surgical instrument 10 to more precisely control the movement of the surgical instrument 10. The surgical instrument 10 may be configured to send the measurements gathered by the first and second pressure sensors 60a, 60b of the end effector 20 to an interface of the robotic surgical system on which the measurements may be displayed for the clinician to read.

Figure 4:
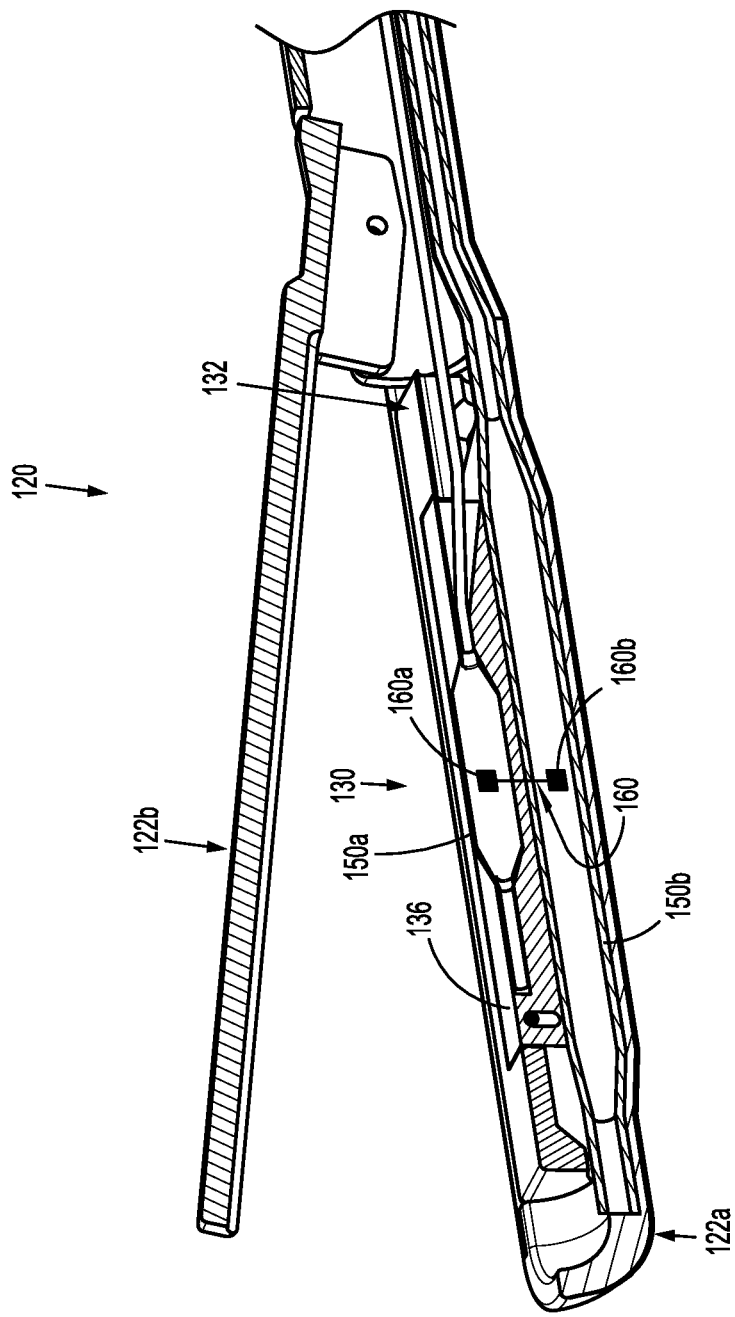
FIG. 4 is a cross-sectional view of another embodiment of an end effector for grasping tissue and determining a local blood pressure of the grasped tissue.

With reference to FIG. 4, another embodiment of an end effector 120 is provided. The end effector 120 is similar to the end effector 20 described with reference to FIGS. 1-3A, and will therefore only be described with the detail necessary to elucidate any differences. The end effector 120 includes a pair of opposing jaw members 122a, 122b and a blood pressure sensing assembly 130 disposed in a first jaw member 122a of the pair of jaw members 122a, 122b.

Similar to the pressure sensing assembly 30 described above, the pressure sensing assembly 130 of the presently described embodiment includes a piston 136 movably disposed within a housing 132, and first and second inflatable members 150a, 150b. However, instead of each of the first and second inflatable members 150a, 150b having discreet pressure sensors, a dual-function pressure sensor 160 is provided that extends through each of the first and second inflatable members 150a, 150b.

In particular, the dual-function pressure sensor 160 includes a first portion 160a disposed within the first inflatable member 150a, and a second portion 160b extending within the second inflatable member 150b. The first portion 160a of the pressure sensor assembly 160 is configured as a first pressure sensor (e.g., a piezoelectric transducer, a piezoresistive strain gauge, an electromagnetic optical sensor, etc.) that detects pressure variations within the first inflatable member 150a caused by pulse waves generated by the pulsatile flow of blood through an artery (e.g., oscillations). The second portion 160b of the dual-function pressure sensor 160 is configured as a second pressure sensor (e.g., a piezoresistive pressure sensor, a capacitive pressure sensor, a MEMS device, etc.), which measures the pressure (e.g., air pressure) within the second inflatable member 150b. The end effector 120 may determine blood pressure in grasped tissue using the measurements taken by the sensor 160 in a similar manner as that described above with respect to the end effector 20.

Although the illustrative embodiments of the present disclosure have been described herein, it is understood that the disclosure is not limited to those precise embodiments, and that various other changes and modifications may be affected therein by one skilled in the art without departing from the scope or spirit of the disclosure. For example, while described with respect to a grasper, it is envisioned that a blood pressure sensing assembly in accordance with the present disclosure may be incorporated into other surgical instruments, such as, for example, surgical staplers. All such changes and modifications are intended to be included within the scope of the disclosure.

The invention claimed is:

1. An end effector for determining blood pressure, comprising:
   a pair of jaw members, a first jaw member of the pair of jaw members including:
      a jaw body;
      a piston coupled to the jaw body and configured to move relative to the jaw body to apply pressure to tissue disposed between the pair of jaw members;
      a first inflatable member coupled to the piston;
      a first pressure sensor associated with the first inflatable member, the first pressure sensor configured to detect pressure fluctuations caused by blood flowing through tissue disposed between the pair of jaw members; and
      a second inflatable member disposed adjacent the piston such that the second inflatable member moves the piston and the first inflatable member upon being inflated.

2. The end effector according to claim 1, wherein the first pressure sensor is further configured to determine a pressure within the first inflatable member.

3. The end effector according to claim 1, wherein the first jaw member further includes a second pressure sensor associated with the second inflatable member, the second pressure sensor configured to determine a pressure within the second inflatable member.

4. The end effector according to claim 1, wherein the first pressure sensor has a first portion in communication with an interior of the first inflatable member, and a second portion in communication with an interior of the second inflatable member, the second portion of the first pressure sensor being configured to determine a pressure within the second inflatable member.

5. The end effector according to claim 1, wherein the piston has an elongated configuration and defines a hole having the first inflatable member captured therein.

6. The end effector according to claim 1, wherein the first jaw member further includes a housing fixed within the jaw body, the housing defining an opening having the piston movably disposed therein.

7. The end effector according to claim 1, wherein the piston is configured to move relative to the jaw body between a first position and at least one second condition, in which the piston protrudes a greater distance relative to the jaw body than in the first position.

8. A surgical instrument for determining blood pressure, comprising:
   a handle portion;
   a shaft coupled to the handle portion; and
   a pair of jaw members operably coupled to the shaft, a first jaw member of the pair of jaw members including:
      a jaw body;
      a piston coupled to the jaw body and configured to move relative to the jaw body to apply pressure on tissue disposed between the pair of jaw member;
      a first inflatable member coupled to the piston, wherein the piston defines a hole having the first inflatable member disposed therein; and
      a first pressure sensor associated with the first inflatable member, the first pressure sensor configured to detect pressure fluctuations caused by blood flowing through tissue disposed between the pair of jaw members.

9. The surgical instrument according to claim 8, wherein the first pressure sensor is further configured to determine a pressure within the first inflatable member.

10. The surgical instrument according to claim 8, wherein the first jaw member further includes a second inflatable member disposed adjacent the piston such that the second inflatable member moves the piston and the first inflatable member upon being inflated with an inflation medium.

11. The surgical instrument according to claim 10, wherein the first jaw member further includes a second pressure sensor associated with the second inflatable member, the second pressure sensor being configured to determine a pressure within the second inflatable member.

12. The surgical instrument according to claim 10, wherein the first pressure sensor has a first portion in communication with an interior of the first inflatable member, and a second portion in communication with an interior of the second inflatable member, the second portion of the first pressure sensor being configured to determine a pressure within the second inflatable member.

13. The surgical instrument according to claim 10, wherein the piston is coupled to the second inflatable member such that the piston moves away from the jaw body in response to an expansion of the second inflatable member and the piston moves toward the jaw body in response to a contraction of the second inflatable member.

14. The surgical instrument according to claim 8, further comprising a processor in communication with the first pressure sensor, the processor being configured to calculate a blood pressure of tissue grasped by the pair of jaw members based on the pressure fluctuations detected by the first pressure sensor.

15. The surgical instrument according to claim 8, wherein the first jaw member further includes a housing fixed within the jaw body, the housing defining an opening having the piston movably disposed therein.

16. The surgical instrument according to claim 8, wherein the piston is configured to move relative to the jaw body between a first position and at least one second condition, in which the piston projects a greater distance relative to the jaw body than in the first position.

17. The surgical instrument according to claim 8, wherein the surgical instrument is laparoscopic, and the pair of jaw members are movable relative to one another between spaced and approximated positions in response to an actuation of the handle portion.

18. A method of determining local blood pressure, comprising:
- positioning tissue between a pair of jaw members of a surgical instrument;
- moving a piston having a first inflatable member associated therewith relative to a jaw body of a first jaw member of the pair of jaw members, thereby applying pressure on the tissue with at least one of the piston or the first inflatable member;
- measuring pressure fluctuations in the first inflatable member with a first pressure sensor associated with the first inflatable member; and
- determining, using the measured pressure fluctuations, the local blood pressure of the tissue, wherein the piston is moved by expanding a second inflatable member of the first jaw member.

19. The method according to claim 18, further comprising determining a pressure within the second inflatable member as the piston is being moved, wherein the local blood pressure of the tissue is determined using both the measured pressure fluctuations in the first inflatable member and the measured pressure within the second inflatable member.

20. The method according to claim 18, further comprising moving the piston and the first inflatable member toward the jaw body to reduce the applied pressure on the tissue, wherein the first pressure sensor measures the pressure fluctuations as the pressure applied on the tissue is reduced.

21. The method according to claim 18, further comprising contracting the second inflatable member to move the piston and the first inflatable member toward the jaw body, thereby reducing the pressure applied on the tissue by the piston.

* * * * *